United States Patent [19]

Imai et al.

[11] 4,423,219
[45] Dec. 27, 1983

[54] PRODUCTION OF PURINE DERIVATIVES AND INTERMEDIATES THEREFOR

[75] Inventors: Kin-ichi Imai, Toyonaka; Mitsuhiko Mano, Suita, both of Japan

[73] Assignee: Takeda Chemical Industries, Ltd., Osaka, Japan

[21] Appl. No.: 318,277

[22] Filed: Nov. 4, 1981

[30] Foreign Application Priority Data

Nov. 14, 1980 [JP] Japan .................................. 55-161099
Aug. 18, 1981 [JP] Japan .................................. 56-129518

[51] Int. Cl.³ .......................................... C07D 239/50
[52] U.S. Cl. ................................... 544/326; 544/277
[58] Field of Search .......................................... 544/326

[56] References Cited

U.S. PATENT DOCUMENTS 3,856,772 12/1974 Dunkelmann et al. ............. 544/326
4,092,314 5/1978 Vander Zwan et al. ........... 544/277

OTHER PUBLICATIONS

Vander Zwan et al., Chem. Abs., vol. 89: 146926r (1978).

*Primary Examiner*—Mary C. Lee
*Attorney, Agent, or Firm*—Wenderoth, Lind & Ponack

[57] ABSTRACT

Improved processes for producing purine derivatives, such as 9-(2-chloro-6-fluorobenzyl)-6-methylaminopurine, which are useful as anticoccidial agents, and new arylazopyrimidine compounds of the formula:

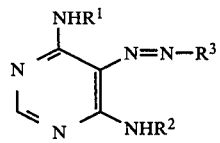

wherein $R^1$ and $R^2$ each is hydrogen, $C_{1-3}$alkyl, allyl or dihalobenzyl, and when either one of $R^1$ and $R^2$ is hydrogen, the other is other than hydrogen, and $R^3$ is aryl, and acid addition salts thereof, which are useful as intermediates for production of the purine derivatives.

1 Claim, No Drawings

PRODUCTION OF PURINE DERIVATIVES AND INTERMEDIATES THEREFOR

This invention relates to new processes for producing purine derivatives and relates to new arylazopyrimidine compounds which are useful as intermediates for production of the purine derivatives.

More particularly, this invention provides new arylazopyrimidine compounds of the formula:

wherein $R^1$ and $R^2$ each is hydrogen, $C_{1-3}$alkyl, allyl or dihalobenzyl of the formula:

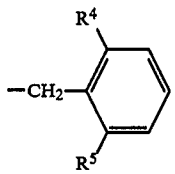

wherein $R^4$ and $R^5$ each is halogen, and when either one of $R^1$ and $R^2$ is hydrogen, the other is other than hydrogen, and
$R^3$ is aryl,
and acid addition salts thereof.

Referring to formula (I), the $C_{1-3}$ alkyl group represented by $R^1$ and $R^2$ may for example be methyl, ethyl, propyl, isopropyl, etc., and methyl is especially desirable. When one of $R^1$ and $R^2$ is H, the other is a group other than H, i.e. $C_{1-3}$ alkyl, allyl or dihalobenzyl. The aryl group $R^3$ may for example be phenyl, tolyl or the like, and phenyl is especially desirable. The halogen atoms $R^4$ and $R^5$ in the dihalobenzyl group may for example be chlorine, fluorine or/and the like. It is preferred that one of $R^4$ and $R^5$ is Cl with the other being F.

The compound (I) of this invention can be produced, for example, by reacting an arylazomalononitrile compound of formula (II):

$$R^3-N=N-CH(CN)_2 \quad (II)$$

[$R^3$ is as defined above],
with a formamide commpound of formula (III):

$$HCONHR^1 \quad (III)$$

[$R^1$ is as defined above],
and an amine compound of formula (IV):

$$R^2NH_2 \quad (IV)$$

[$R^2$ is as defined above].

Sometimes, the above reaction proceeds more satisfactorily when a part or all of compound (IV) is used in the form of a salt with an acid (e.g. hydrochloride). In lieu of (IV), the formamide compound corresponding to (IV) and a base (e.g. dimethylamine, diethylamine, trimethylamine, triethylamine, tripropylamine, potassium hydroxide, sodium hydroxide) may be employed. In such a case, it is likely that the reaction of formamide with base yields an amine compound (IV) as an intermediate in situ and this amine (IV) then reacts with (II) and (III).

The reaction is usually conducted in a closed reaction system at a temperature from about 120° to 160° C. (preferably about 150° C.) for about 1 to 10 hours (preferably about 5 hours).

The compounds produced by the above-mentioned reaction may be represented by the formula (Ia):

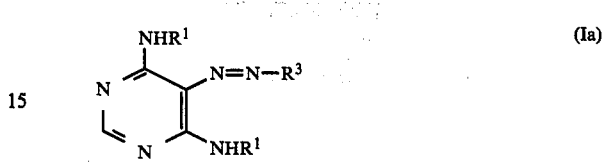

[$R^1$ and $R^3$ are as defined hereinbefore] or the formula (Ib):

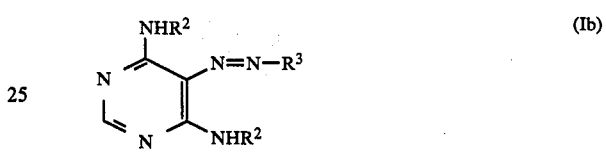

[$R^2$ and $R^3$ are as defined hereinbefore], depending on the combination of starting materials employed, but, even in such case, these compounds are all, needless to say, within the scope covered by the formula (I), because definitions of $R^1$ and $R^2$ are of the same coverage.

The following lists are examples of reactants. The ratio given under each set of reactants represents their molar ratio to be employed.

---

1. Production of 4-amino-6-(substituted amino)pyrimidines
   (1) (II) + HCONHR$^1$ + NH$_3$
       1:1–50:1–100
   (2) (II) + HCONH$_2$ + HCONHR$^1$ + base
       1:10–50:10–50:1–10
   (3) (II) + HCONH$_2$ + R$^2$NH$_2$
       1:10–50:1–100
   (4) (II) + HCONH$_2$ + R$^2$NH$_2$ + R$^2$NH$_2$.HCl
       1:10–50:1–100:0.2–30
   (5) (II) + HCONH$_2$ + HCONHR$^1$ + R$^2$NH$_2$ + R$^2$NH$_2$.HCl[R$^1$=R$^2$]
       1:10–50:10–30:1–100:0.2–30
2. Production of 4,6-bis(substituted amino)pyrimidines
   (1) (II) + HCONHR$^1$ + R$^2$NH$_2$ [R$^1$=R$^2$]
       1:10–50:1–100
   (2) (II) + HCONHR$^1$ + R$^2$NH$_2$ + R$^2$NH$_2$.HCl [R$^1$=R$^2$]
       1:10–50:1–100:1–10
   (3) (II) + HCONH$_2$ + R$^2$NH$_2$ + R$^2$NH$_2$.HCl
       1:10–50:10–100:1–10
   (4) (II) + HCONHR$^1$ + NH$_3$
       1:10–50:1–100
3. Production of 4,6-di(substituted amino)pyrimidines
   (1) (II) + HCONHR$^1$ + R$^2$NH$_2$
       1:1–20:1–50
   (2) (II) + HCONHR$^1$ + R$^2$NH$_2$ + R$^2$NH$_2$.HCl
       1:1–20:1–50:0.1–1

---

The compounds (I) thus produced can be separated and purified from the reaction mixture by a conventional procedure (e.g. column chromatography, filtration, recrystallization). Also, the compounds (I) can be isolated in the form of a salt, for example an acid addition salt (e.g., hydrochloride, sulfate).

The compounds (I) of this invention are new compounds and because they can be readily converted to adenine or various purine derivatives having anticoccidial activity (U.S. Pat. Nos. 3,846,426, 4,189,485) by, for example, the following new procedures, it is of great commercial value as an intermediate for the production of such compounds.

(a)

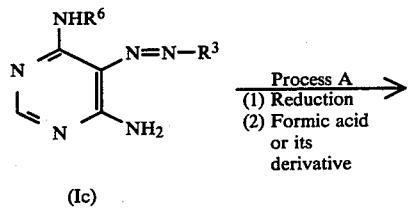

(Ic)

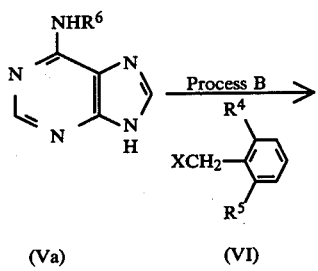

(Va)    (VI)

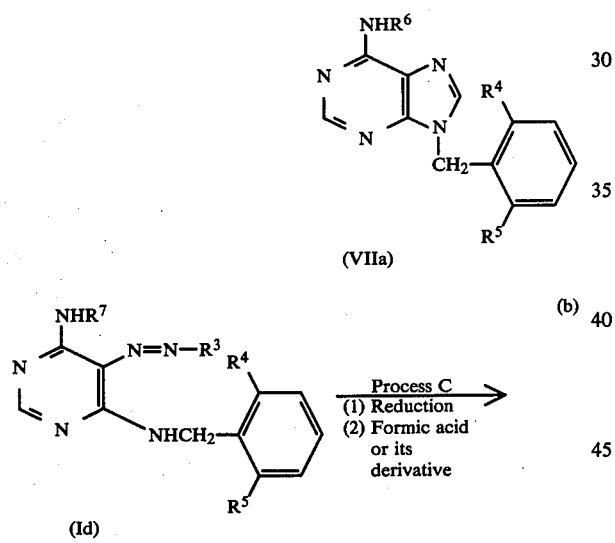

(VIIa)

(b)

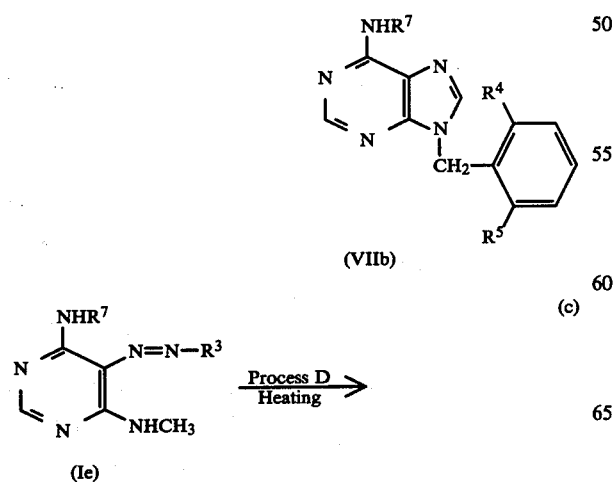

(Id)

(VIIb)

(c)

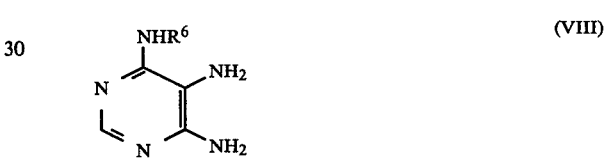

(Ie)

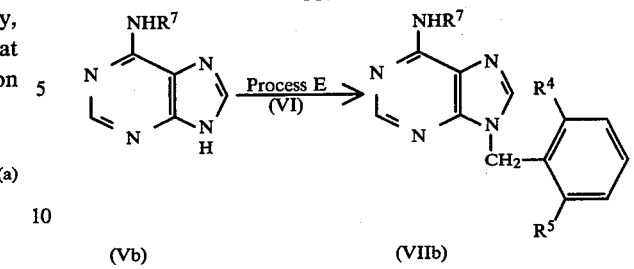

(Vb)    (VIIb)

[In the above formulas, $R^6$ is $C_{1-3}$ alkyl or allyl as defined for $R^1$ and $R^2$; $R^7$ is H, $C_{1-3}$ alkyl or allyl as defined for $R^1$ and $R^2$; X is halogen (e.g. Cl, Br); the other symbols are as defined hereinbefore.]

Each of the above reaction processes will hereinafter be described in detail.

The reaction of Process A may be carried out by subjecting the compound (Ic) to reduction and, then, reaction with formic acid or its derivatives in the presence of a carboxylic acid derivative to give the compound (Va).

Thus, it is considered that the reduction of the pyrimidine derivative (Ic) forms a compound of the formula:

$$\text{(VIII)}$$

[structure of compound VIII with $NHR^6$, $NH_2$, $NH_2$ substituents]

[wherein $R^6$ is as defined above] and the compound (VIII) is cyclized by reaction with formic acid or its derivative in the presence of a carboxylic acid derivative to give the compound (Va).

The reduction of the compound (Ic) may be conducted by catalytic reduction or reduction with sodium dithionite, sodium sulfide or the like. The catalytic reduction is carried out in a solvent such as methanol, ethanol, formamide, N-methylformamide, etc. The catalyst includes palladium, palladium on carbon, Raney nickel, etc. The reduction is conducted at room temperature or under heating up to 150° C. and at atmospheric or supratmospheric pressure.

It is not always necessary to effect the reduction and ring closure reactions stepwise and it is also possible to obtain the compound (Va) in a single step, for example, by carrying out the cyclization reaction under reducing conditions.

The carboxylic acid derivative that is used in the cyclization reaction includes various carboxylic acid derivatives which are conventionally used in acylation, for example, acid anhydrides (e.g., acetic anhydride, formicacetic anhydride), acid halides (e.g., acetyl chloride, benzoyl chloride), etc. Of these, acetic anhydride is preferably used. The carboxylic acid derivatives serve to promote the ring closure reaction between the two amino groups at the 4- and 5-positions of the compound (VIII) and to prevent ring closure in another direction.

The derivative of formic acid includes, for example, ethyl orthoformate, formamide, ethyl formate, etc., and particularly ethyl orthoformate is preferably used.

The ring closure can be effected by adding about 2 to 20 weights of formic acid or its derivative and similarly about 2 to 20 weights of a carboxylic acid derivative to the compound (VIII) and heating the mixture under reflux for about 1 to 5 hours.

The resulting reaction mixture may be heated under alkaline conditions (e.g., by addition of aqueous sodium hydroxide) and neutralized with an acid (e.g., acetic acid) to precipitate the compound (Va).

The reaction of Process B may be carried out by reacting the compound (Va) with the compound (VI) in the presence of a base. This benzylation may be conducted in a two-phase system of liquid-liquid or solid-liquid in the presence of a phase transfer catalyst. A base may be present in the reaction system or alternatively the compound (Va) may be used in the form of its salt with an alkali metal as a kind of base. Accordingly, the following two-phase systems are exemplified:

(1) a two-phase system of an aqueous base solution phase in which the compound (Va) is dissolved and an organic solvent phase in which the compound (VI) is dissolved;

(2) a two-phase system of a solid (powdery) phase consisting of the compound (Va) and a base and an organic solvent phase in which the compound (VI) is dissolved; and (3) a two-phase system of a solid (powdery) phase of an alkali metal salt of the compound (Va) and an organic solvent phase in which the compound (VI) is dissolved.

The base that is used in the reactions in (1) and (2) includes, for example, sodium hydroxide, potassium hydroxide, lithium hydroxide, sodium carbonate, lithium carbonate, sodium ethoxide, etc., and the alkali metal salt in (3) includes those salts derived from the compound (Va) and the above-mentioned bases, for example, sodium salt and potassium salt.

The organic solvent that is used in all the reactions includes, for example, hexane, petroleum ether, benzene, toluene, methylene chloride, 1,2-dichloroethane, acetone, acetonitrile, etc. Of these, hexane, acetone and acetonitrile are preferred.

The phase transfer catalyst that is used in the two-phase reactions includes, for example, quaternary ammonium salts, phosphonium salts, crown ethers, etc.

The hydrocarbon group moieties of the quaternary ammonium salt are preferably alkyl groups having approximately 1 to 20 carbon atoms which may be the same or different. The anion moiety is preferably a halogen, for example. Typical quaternary ammonium salts include, for example, trioctylmethylammonium chloride, hexadecyltrimethylammonium chloride, dodecyltrimethylammonium chloride, tetrabutylammonium bromide, etc.

The phosphonium salt includes, for example, benzyltriphenylphosphnium chloride.

The crown ether includes, for example, 18-crown-6.

Of these phase transfer catalysts, the quatenary ammonium salts are usually employed to advantage.

In each of the above-mentioned benzylation reactions, it is sufficient to use the compound (VI) in an equimolecular or slightly excess (up to 1 mole excess) amount relative to the compound (Va). Based on the compound (Va), the amount of the solvent used is about 5 to 20 times (weight ratio), that of the base is about 1 to 2 moles per mole of the compound, and that of the catalyst is about 0.1 to 20 mol%, preferably around 5 mol%. The reaction temperature is about 0° to 120° C. and particularly a temperature in the range of room temperature to about 70° C. is desirable.

In the reaction (1), it is desirable to use water in as small an amount as possible and the minimum amount required to dissolve (Va) may be preferable.

In the benzylation process, in addition to the desired purine derivative (VIIa), a small amount of its isomer (3-substituted isomer) is usually formed. Since the 3-isomer is more readily soluble in dilute acids as compared with (VIIa) and unstable to strong acids, it can be removed by utilizing these properties thereof. For example, the reaction product may be heated with dilute nitric acid or acetic acid to remove the soluble 3-isomer. The 3-isomer which still remains in a small amount can be removed by suspending the dilute acid-insoluble material in toluene, adding conc. sulfuric acid and heating. This procedure can provide a pure product (VIIa). In addition, by subjecting the 3-isomer in the dilute acid extract to the same procedure as above, the starting material (Va) can be recovered and reused.

The benzylation of Process B as mentioned above is advantageous in that the reaction is allowed to proceed very effectively in a conventional inexpensive solvent by the addition of a phase transfer catalyst without use of an aprotic dipolar solvent such as N,N-dimethylformamide, N,N-dimethylacetamide, dimethyl sulfoxide, etc. which have heretofore been used widely in this type of reactions and are expensive and troublesome to recover, and also in that the desired product (VIIa) can be prepared in high yields.

Accordingly, the present process is advantageous and suitable for commercial operation.

The benzylation of Process B may also be conducted in a conventional inert solvent in the presence of a base. As examples of said base, there may be mentioned tertiaryamines (e.g. trimethylamine, triethylamine, tripropylamine) in addition to those in the two-phase reaction. The amount of the base is preferably about 1 to 4 molar equivalents to that of the compound (Va). Examples of the solvent include N,N-dimethylformamide, N,N-dimethylacetamide, acetonitrile, nitromethane, alcohols (e.g. methanol, ethanol, tertiarybutanol) and the like. The reaction may be carried out at a temperature from room temperature to about 150° C., preferably at a temperature from about 50° C. to about 110° C. The amount of the compound (VI) is preferably 1 to 4 molar equivalents to that of the compound (Va).

The reaction of Process C may be carried out by subjecting the compound (Id) to reduction and, then, reaction with formic acid or its derivative to give the compound (VIIb). This reaction is conducted under conditions almost similar to those described for Process A. In the reduction step, an intermediate compound (VIII') similar to (VIII) is likely to be produced.

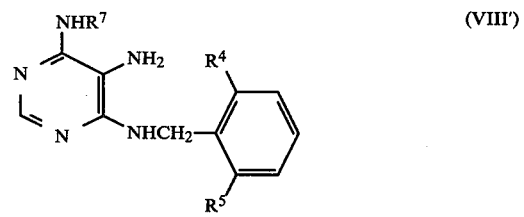

(VIII')

[wherein all the symbols are as defined hereinbefore]. The reaction mixture containing this intermediate compound, or the intermediate compound isolated from the mixture, is then caused to undergo cyclization to yield (VIIb). In this Process C, catalytic reduction is not a desirable reduction method. Reduction with sodium dithionite or sodium sulfide is preferred. In the cyclization step of this process, unlike Process A mentioned earlier, a carboxylic acid derivative need not be present in the reaction system.

In Process D, (Ie) is cyclized under heating to give (Vb).

This cyclization reaction is carried out by heating (Ie) as such at 200°–300° C. for 5–30 minutes, or by suspending or dissolving (Ie) in a solvent such as nitrobenzene or Dowtherm, for instance, and heating the suspension or solution for 1–5 hours. By way of illustration, when $R^7$ of (Ie) is methyl, heating the compound (Ie) in the absence of a solvent at 250°–260° C. for about 10 minutes, and when $R^7$ is H, heating (Ie) in Dowtherm under reflux for about 2 hours give the most satisfactory result.

The reaction of Process E may be carried out by reacting (Vb) with (VI) in the presence of a base to give (VIIb). This Process E may be conducted under the same conditions as those of Process B mentioned hereinbefore except that (Vb) is used in lieu of (Va) of Process B and (VIIb) is produced in liue of (VIIa).

The resulting compounds (VIIa) and (VIIb) are of value, for example as anticoccidial agents as described in Japanese Patent Unexamined Publication (Kokai) Nos. 47-29394 and 54-36292 which correspond to U.S. Pat. Nos. 3,846,426 and 4,189,485, respectively. Therefore, by utilizing the new pyrmidine compounds (I) of this invention as intermediates, anticoccidial agents can be produced in high yield and in a commercially profitable manner. This invention, in an additional aspect thereof, provides methods for producing such anticoccidial agents. Among the pyrimidine compounds (I) of this invention, 4-amino-6-methylamino-5-phenylazopyrimidine and 4,6-bis(methylamino)-5-phenylazopyrimidine are especially valuable intermediates for the commercial production of 9-(2-chloro-6-fluorobenzyl)-6-methylaminopurine, a very desirable anticoccidial agent known, for each of these compounds (I) can be profitably converted to said anticoccidial agent via 6-methylaminopurine.

The following working examples are intended to illustrate this invention in further detail and should by no means be construed as limiting the scope of the invention.

EXAMPLE 1

In an autoclave, phenylazomalononitrile (42.55 g, 250 mmols), N-methylformamide (245 g, 5 mols) and liquid ammonia (345 ml, 12.5 mol) were stirred together at 150° C. for 5 hours. The reaction mixture was concentrated under reduced pressure and the residue was dissolved in chloroform (1 l). The solution was washed with water, dried over anhydrous magnesium sulfate, and the chloroform was evaporated under reduced pressure. The resultant residue was purified by silica gel column chromatography (900 g, eluent: chloroform) and recrystallized from chloroform-petroleum ether to give 4-amino-6-methylamino-5-phenylazopyrimidine as orange-colored needles (34 g, yield 60%), m.p. 189°–190° C.

EXAMPLE 2

Phenylazomalonitrile (850 mg, 5 mmols) and formamide (4.5 g, 100 mmols) were put in a stainless steel autoclave, followed by addition of 15% ammonia-containing N-methylformamide (6.9 g) and stirring at 150° C. for 5 hours. Thereafter the same procedure as that described in Example 1 was followed to give 4-amino-6-methylamino-5-phenylazopyrimidine as orange-colored needles (270 mg, yield 24%).

EXAMPLE 3

Potassium hydroxide (1.68 g, 30 mmols) was dissolved in formamide (4.5 g, 100 mmols) and N-methylformamide (5.9 g, 100 mmols). The solution was put in a stainless steel autoclave with phenylazomalononitrile (850 mg, 5 mmols) and the mixture was stirred at 150° C. for 5 hours. Thereafter the same procedure as that described in Example 1 was followed to give 4-amino-6-methylamino-5-phenylazopyrimidine as orange-colored needles (184 mg, yield 16%).

EXAMPLE 4

Phenylazomalononitrile (850 mg, 5 mmols), methylamine hydrochloride (675 mg, 10 mmols) and N-methylformamide (5.9 g, 100 mmols) were put in a stainless steel autoclave, followed by addition of 17% methylamine-containing formamide (5.45 g) and stirring at 150° C. for 5 hours. Thereafter the same procedure as that described in Example 1 was followed to give 4-amino-6-methylamino-5-phenylazopyrimidine as orange-colored needles (610 mg, yield 53%).

EXAMPLE 5

Phenylazomalononitrile (850 mg, 5 mmols) and methylamine hydrochloride (675 mg, 10 mmols) were put in a stainless steel autoclave, followed by addition of a 10% methylamine-containing formamide (9.3 g) and stirring at 150° C. for 5 hours. Thereafter the same procedure as that described in Example 1 was followed to give 4-amino-6-methylamino-5-phenylazopyrimidine as orange-colored needles (405 mg, yield 36%).

EXAMPLE 6

In a stainless steel autoclave, phenylazomalonitrile (17.02 g, 100 mmols), 2-chloro-6-fluorobenzylamine (15.96 g, 100 mmols) and formamide (90.08 g, 2 mols) were stirred together at 150° C. for 5 hours. Thereafter, the reaction product was treated in the same manner as Example 1 to give 4-amino-6-(2-chloro-6-fluorobenzyl)amino-5-phenylazopyrimidine as yellow needles (2.6 g, yield 7%), m.p. 178°–180° C.

EXAMPLE 7

A stainless steel autoclave was charged with phenylazomalonitrile (510 mg, 3 mmols) and N-(2-chloro-6-fluorobenzyl)formamide (5.63 g, 30 mmols), followed by addition of liquid ammonia (2.55 g, 150 mmols). The mixture was stirred at 150° C. for 5 hours. The reaction product was then treated in the same manner as Example 1 to give 4-amino-6-(2-chloro-6-fluorobenzyl)amino-5-phenylazopyrimidine as yellow needles (135 mg, yield 13%).

EXAMPLE 8

In a stainless steel autoclave, phenylazomalononitrile (1.7 g, 10 mmols), methylamine (15.53 g, 500 mmols), methylamine hydrochloride (1.35 g, 20 mmols) and formamide (9 g, 200 mmols) were stirred together at 150° C. for 5 hours. The reaction product was then treated in the same manner as Example 1 to give 4,6- bis(methylamino)-5-phenylazopyrimidine as orange-colored crystals (1.711 g, yield 71%), m.p. 128°–129° C.

EXAMPLE 9

In a stainless steel autoclave, phenylazomalononitrile (4.255 g, 25 mmols), methylamine (38.8 g, 1.25 mols) and N-methylformamide (24.5 g, 500 mmols) were stirred together at 150° C. for 5 hours. The reaction product was then treated in the same manner as Example 1 to give 4,6-bis(methylamino)-5-phenylazopyrimidine as orange-colored crystals (2.1 g, yield 35%).

EXAMPLE 10

In a stainless steel autoclave, phenylazomalononitrile (25.53 g, 150 mmols), 2-chloro-6-fluorobenzylamine (47.88 g, 300 mmols), 2-chloro-6-fluorobenzylamine hydrochloride (5.88 g, 30 mmols) and N-methylformamide (44.3 g, 750 mmols) were stirred together at 150° C. for 5 hours. The reaction product was then treated in the same manner as Example 1 to give 6-(2-chloro-6-fluorobenzyl)amino-4-methylamino-5-phenylazopyrimidine as orange-colored crystals (4.217 g, yield 8%), m.p. 139°–141° C.

EXAMPLE 11

Phenylazomalononitrile (850 mg, 5 mmols) and N-methylformamide (5.9 g, 100 mmols) were put in a stainless steel autoclave and cooled with dry ice-acetone. To this was added liquid ammonia (4.25 g, 250 mmols). The mixture was stirred at 150° C. for 5 hours and the reaction mixture was concentrated under reduced pressure, the residue being dissolved in chloroform (100 ml). The solution was washed with water, dried over anhydrous magnesium sulfate, and the solvent was evaporated under reduced pressure. The residue was purified by silica gel column chromatography (30 g, eluent: chloroform) and recrystallized from chloroform-petroleum ether to give 4-amino-6-methylamino-5-phenylazopyrimidine as orange needles (643 mg, yield 56%), m.p. 190°–191° C.

EXAMPLE 12

1. A 1-liter autoclave was charged with 4-amino-6-methylamino-5-phenylazopyrimidine (34.2 g, 150 mmols), 5% palladium on carbon (3 g) and methanol (700 ml) and after introduction of hydrogen gas (initial pressure 80.0 kg/cm²), the reaction was conducted at 7°–42° C. for 3 hours. The catalyst was filtered off and the filtrate was concentrated to dryness under reduced pressure. To the residue was added ethanol-ether (1:5) (200 ml), followed by ice-cooling. The procedure yielded crystals of 4,5-diamino-6-methylaminopyrimidine (17.68 g, yield 85%), m.p. 180°–185° C.

2. In ethyl orthoformate-acetic anhydride (1:1) (250 ml) was suspended 4,5-diamino-6-methylaminopyrimidine (13.92 g, 100 mmols), and the suspension was refluxed with stirring for 3 hours. After cooling, the mixture was concentrated to dryness under reduced pressure and the residue was recrystallized from ethanol to give brown crystals (14.95 g). This product was suspended in 2 N NaOH (150 ml) and the suspension was refluxed for an hour. To the reaction mixture was added glacial acetic acid under ice-cooling to make pH 5. The resulting precipitate was collected by filtration and recrystallized from water to give 6-methylaminopurine as colorless crystals (8.42 g, yield 56%), m.p. >300° C.

3. To a mixture of 6-methylaminopurine (7.45 g, 50 mmols), potassium carbonate (6.9 g, 50 mmols) and N,N-dimethylacetamide (250 ml) was added 2-chloro-6-fluorobenzyl chloride (17.9 g, 100 mmols), and the resultant mixture was allowed to react at 110° C. for 6 hours with stirring. After cooling, the reaction mixture was filtered to remove insoluble materials and the filtrate was concentrated to dryness under reduced pressure. Upon addition of water to the resultant residue, the formed precipitate was collected by filtration and recrystallized from ethanol to give 9-(2-chloro-6-fluorobenzyl)-6-methylaminopurine as colorless needles (9.08 g, yield 63%), m.p. 188°–190° C.

EXAMPLE 13

1. In 2 N NaOH (20 ml) was dissolved 6-methylaminopurine (5.966 g, 40 mmols) and the solution was concentrated to dryness under reduced pressure at 50° C. The concentrate was dried under reduced pressure at 90° C. to give 6-methylaminopurine sodium salt as crystalline powder (7.305 g, purity 94%), m.p. >300° C.

2. In acetone (30 ml) was suspended 6-methylaminopurine sodium salt (3.65 g, 20 mmols, purity 94%) followed by addition of a solution of 2-chloro-6-fluorobenzyl chloride (3.58 g, 20 mmols) and trioctylmethylammonium chloride (404 mg, 1 mmol) in acetone (15 ml), and the mixture was refluxed with stirring for 6 hours. After cooling, the resulting crystals were collected by filtration and washed with acetone (2×10 ml). The crystals were put in water (30 ml), and after stirring for 30 minutes, filtration of the mixture gave crystals of 2-chloro-6-fluorobenzyl-substituted 6-methylaminopurine (4.55 g, yield 78%), 9-isomer 73% (determined by high pressure liquid chromatography assay), 3-isomer 21% (determined by U.V. assay).

From the mother liquor there were obtained crystals of 2-chloro-6-fluorobenzyl-substituted 6-methylaminopurine (696 mg, yield 12%), 9-isomer 102%, 3-isomer 4%.

To the crystals (3.5 g, 9-isomer 73%, 3-isomer 21%) obtained by the above procedure were added water (50 ml) and 1 N nitric acid (2.25 ml), and the mixture was refluxed with stirring for 2 hours. When hot the insoluble matter was collected by filtration and washed with hot water, 28% aqueous ammonia and hot water in that order to give crystals of 2-chloro-6-fluorobenzyl-substituted 6-methylaminopurine (2.7 g), 9-isomer 100%, 3-isomer 3%.

This product (2 g) was suspended in toluene (4 ml), followed by addition of conc. sulfuric acid (4 ml) under ice-cooling and stirring and the mixture further stirred at 50°–60° C. for 18 hours. After cooling, ice water (15 ml) was added and the mixture was warmed to 80°–85° C. The separated aqueous layer was taken, washed with hot toluene (2 ml) and filtered. The filtrate was adjusted to pH 10 by addition of 28% aqueous ammonia and the resulting crystalline precipitate was collected by filtration and washed with hot water to give 9-(2-chloro-6-fluorobenzyl)-6-methylaminopurine as colorless crystals (1.84 g, yield 55%), m.p. 189°–190° C.

EXAMPLE 14

Recovery of 6-methylaminopurine

In toluene (2 ml) was suspended 2-chloro-6-fluorobenzyl-substituted 6-methylaminopurine (1 g; 3-isomer 92%, 9-isomer 9%), followed by addition of conc. sulfuric acid (2 ml) under ice-cooling with stirring, and the mixture was further stirred at 50°–60° C. for 18 hours.

The resulting crystals were dissolved under warming and water (6 ml) was added to the solution portionwise. After heating to 80° C., the toluene layer was separated, and the aqueous layer was washed with toluene (5 ml) and filtered. The filtrate was adjusted to pH 10 by addition of 28% aqueous ammonium when hot, filtered once, and adjusted to pH 7 by addition of conc. hydrochloric acid. After cooling, the resulting crude crystals were collected by filtration aand recrystallized from ethanol to give 6-methylaminopurine as crystals (190 mg, yield 40%) m.p.>300° C.

EXAMPLE 15

1. 4,6-Bis(methylamino)-5-phenylazopyrimidine (18 g, 74 mmols) was heated at 250°–260° C. for 10 minutes. After cooling, methanol (30 ml) and water (30 ml) were added to dissolve the resulting material. Separation and purification by silica gel column chromatography [950 g, eluent: acetone-water (49:1)] gave two fractions.

Fraction I was concentrated to dryness under reduced pressure, and the residue was dissolved in methanol (200 ml) under heating. The solution was treated with activated carbon and concentrated to dryness under reduced pressure. To the crystalline residue was added acetone (50 ml), and the mixture was refluxed for 30 minutes. After cooling, the crystals (1.2 g) were collected by filtration and recrystallized from water to give 6-methylaminopurine as colorless crystals (1.036 g, yield 9%), m.p.>300° C.

Fraction II was concentrated to dryness under reduced pressure and dissolved in methanol-water (1:1, 50 ml). Then, separation and purification by silica gel column chromatography (800 g) was conducted. The resulting product was treated in the same manner as above to give 6-methylaminopurine as colorless crystals (1.25 g, yield 11%). The combined yield of crystals from Fractions I and II: 2.286 g or 21%.

2. To a mixture of 6-methylaminopurine (298 mg, 2 mmols), potassium carbonate (276 mg, 2 mmols) and N,N-dimethylacetamide (10 ml) was added 2-chloro-6-fluorobenzyl chloride (718 mg, 4 mmols), and the resultant mixture was allowed to react at 110° C. for 8 hours with stirring. The reaction product was then treated in the same manner as Example 12 to give 9-(2-chloro-6-fluorobenzyl)-6-methylaminopurine as needles (320 mg, yield 55%), m.p. 188°–190° C.

EXAMPLE 16

In Dowtherm (a mixture of 73.5% of diphenyl ether and 26.5% diphenyl) (20 ml) was suspended 4-amino-6-methylamino-5-phenylazopyrimidine (10 g, 44 mmols), and the suspension was refluxed with stirring for 2 hours. After cooling, ether (300 ml) was added to the reaction mixture and the insoluble matter was collected by filtration. This product was dissolved in a mixture of methanol (100 ml) and water (100 ml). Separation and purification in the same manner as Example 15 gave colorless crystals of adenine (828 mg, yield 14%).

EXAMPLE 17

In formamide (60 ml) was suspended 4-amino-6-(2-chloro-6-fluorobenzyl)amino-5-phenylazopyrimidine (1.07 g, 3 mmols). To the suspension was added portionwise sodium dithionite (3.28 g, 15 mmols; purity 80%) with stirring at 120°–130° C. After stirring at the same temperature for 30 minutes, the mixture was stirred at 140°–150° C. for another 1 hour. The reaction mixture was concentrated to dryness under reduced pressure, the residue washed with ether (2×30 ml), and water (50 ml) added. After ice-cooling, the insoluble matter was collected by filtration and washed. This product was put in 2 N NaOH (10 ml) and the mixture was stirred at room temperature for 30 minutes. The insoluble matter was collected by filtration, dissolved in chloroform, and purified by silica gel column chromatography [100 g, eluent: chloroform and, then, chloroformmethanol (19:1)]. Recrystallization from ethanol gave 6-amino-9-(2-chloro-6-fluorobenzyl)purine as colorless crystals (350 mg, yield 42%), m.p. 249°–250° C.

EXAMPLE 18

1. In N,N-dimethylformamide (20 ml) and 2 N NaOH (5 ml) was dissolved 4-(2-chloro-6-fluorobenzyl)amino-6-methylamino-5-phenylazopyrimidine (1.112 g, 3 mmols), and sodium dithionite (3.27 g, 15 mmol; purity 80%) was added portionwise to the solution with stirring at 140°–150° C. The mixture was stirred at the same temperature for 30 minutes, after which it was concentrated to dryness under reduced pressure, and water was added to the residue. The mixture was adjusted to pH 12–13 by addition of 2 N NaOH, and extracted with ethyl acetate (150 ml, 100 ml). The extract was dried over anhydrous sodium sulfate. The ethyl acetate was evaporated under reduced pressure, and the resultant residue was recrystallized from ethyl acetate-petroleum ether to give 5-amino-4-(2-chloro-6-fluorobenzyl)amino-6-methylaminopyrimidine as brown crystals (671 mg, yield 79%), m.p. 210°–213° C.

2. To 5-amino-4-(2-chloro-6-fluorobenzyl)amino-6-methylaminopyrimidine (686 mg, 2.4 mmols) was added formic acid (34 ml, purity 99%) and the mixture was refluxed for 1 hour. The reaction mixture was concentrated to dryness under reduced pressure and the residue was crystallized by addition of ethyl acetate (5 ml). The mixture was diluted with petroleum ether (20 ml) and the product was collected by filtration to give crystals (854 mg). The crystals were heated to 210°–220° C. for 10 minutes, dissolved in chloroform, and purified by silica gel column chromatography (80 g, eluent: chloroform) to give 9-(2-chloro-6-fluorobenzyl)-6-methylaminopurine as crystals (53 mg, yield 7%), m.p. 187°–188° C.

EXAMPLE 19

In water (0.28 ml) was dissolved sodium hydroxide (280 mg, 7 mmols), followed by addition of acetone (14 ml) and 6-methylaminopurine (1.044 g, 7 mmols). The mixture was refluxed in a nitrogen gas stream with stirring for 1.5 hours. After cooling, a solution of 2-chloro-6-fluorobenzyl chloride (1.253 g, 7 mmols) and trioctylmethylammonium chloride (141 mg, 0.35 mmol) in acetone (5 ml) was added and the mixture was refluxed with stirring in a nitrogen gas stream for 6 hours. The reaction mixture was allowed to stand overnight and the resultant crude crystals were collected by filtration and washed with acetone. The crystals were put in water (10 ml), stirred for 30 minutes, and collected by filtration to give crystals of 2-chloro-6-fluorobenzyl-substituted 6-methylaminopurine (1.595 g, yield 78%). 9-Isomer: 65% and 3-isomer: 32%.

The mother liquor remaining after collection of crude crystals was concentrated to dryness under reduced pressure, hexane (20 ml) was added to the residue and the crystals were collected by filtration. The crystals were put in 0.1 N NaOH (5 ml), and stirred for 30 minutes. The crystals were collected by filtration and washed with water to give crystals of 2-chloro-6-fluorobenzyl-substituted 6-methylaminopurine (279 mg, yield 14%). 9-Isomer: 84%, 3-isomer: 4%.

EXAMPLE 20

In water (1.4 ml) was dissolved sodium hydroxide (280 mg, 7 mmols) and, then, 6-methylaminopurine (1.044 g, 7 mmols) was added and dissolved. To this solution was added a solution of 2-chloro-6-fluorobenzyl chloride (1.253 g, 7 mmols) and trioctylmethylammonium chloride (141 mg, 0.35 mmol) in hexane (8.5 ml). Thereafter the same procedure as that described in Example 19 was followed to obtain crystals of 2-chloro-6-fluorobenzyl-substituted 6-methylaminopurine (2.074 g). 9-isomer: 56%, 3-isomer: 32%.

EXAMPLE 21

In water (1.4 ml) was dissolved sodium hydroxide (280 mg, 7 mmols) and, then, 6-methylaminopurine (1.044 g, 7 mmols) was added and dissolved. To this solution was added a solution of 2-chloro-6-fluorobenzyl chloride (1.253 g, 7 mmols) and trioctylmethylammonium chloride (141 mg, 0.35 mmol) in toluene (8.5 ml) and the mixture was refluxed with stirring in a nitrogen gas stream for 6 hours. The reaction mixture was cooled to room temperature and the resultant crude crystals were collected by filtration and washed with toluene. The crystals were put in 0.1 N NaOH (10 ml), and stirred for 30 minutes. The crystals were collected by filtration and washed with water to give crystals of 2-chloro-6-fluorobenzyl-substituted 6-methylaminopurine (1.790 g, yield 88%). 9-isomer 50%, 3-isomer 46%.

EXAMPLE 22

In water (2.8 ml) was dissolved potassium carbonate (967 mg, 7 mmols) followed by addition of acetone (14 ml) and 6-methylaminopurine (1.044 g, 7 mmols) and the mixture was refluxed in a nitrogen gas stream with stirring for 1.5 hours. After cooling, a solution of 2-chloro-6-fluorobenzyl chloride (1.253 g, 7 mmols) and trioctylmethylammonium chloride (141 mg, 0.35 mmol) in acetone (5 ml) was added to the reaction mixture. Thereafter the same procedure as that described in Example 21 was followed to obtain crystals of 2-chloro-6-fluorobenzyl-substituted 6-methylaminopurine (1.106 g, yield 54%). 9-isomer 52%, 3-isomer 42%. The mother liquor was treated in the same manner as in Example 19 to give crystals of 2-chloro-6-fluorobenzyl-substituted 6-methylaminopurine (633 mg, yield 31%). 9-isomer 70%, 3-isomer 15%.

EXAMPLE 23

In acetonitrile (5 ml) were suspended 6-methylaminopurine (1.044 g, 7 mmols) and potassium carbonate (967 mg, 7 mmols) followed by addition of a solution of 2-chloro-6-fluorobenzyl chloride (1.253 g, 7 mmols) and trioctylmethylammonium chloride (141 mg, 0.35 mmol) in acetonitrile (10 ml). Thereafter the same procedure as that described in Example 19 was followed to obtain crystals of 2-chloro-6-fluorobenzyl-substituted 6-methylaminopurine (1.687 g, yield 83%). 9-isomer 66%.

The mother liquor remaining after collection of crude crystals was concentrated to dryness under reduced pressure. To the residue were added hexane (10 ml) and water (10 ml) and the mixture was stirred for 30 minutes. The crystals were collected by filtration and washed with acetone-water (1:1) to give 2-chloro-6-fluorobenzyl-substituted 6-methylaminopurine (162 mg, yield 8%). 9-isomer 65%, 3-isomer 13%.

EXAMPLE 24

In water (0.28 ml) was dissolved sodium hydroxide (280 mg, 7 mmols) followed by addition of acetone (14 ml) and 6-dimethylaminopurine (1.142 g, 7 mmols). The mixture was refluxed in a nitrogen gas stream with stirring for 1.5 hours. After cooling, a solution of 2-chloro-6-fluorobenzyl chloride (1.253 g, 7 mmols) and trioctylmethylammonium chloride (141 mg, 0.35 mmol) in acetone (5 ml) was added to the mixture. Thereafter the same procedure as that described in Example 22 was followed to obtain crystals of 2-chloro-6-fluorobenzyl-substituted 6-dimethylaminopurine (1.146 g, yield 54%). 9-isomer 79%.

From the mother liquor, there was obtained 2-chloro-6-fluorobenzyl substituted 6-dimethylaminopurine (847 mg, yield 40%). 9-isomer 29%.

To the crystals (9-isomer 79%) (500 mg) obtained as above were added water (8 ml) and 1 N nitric acid (0.32 ml) and the mixture was refluxed with stirring for 2 hours. When hot, the insoluble crystals were recovered by filtration and washed with hot water, 28% aqueous ammonia, and hot water in that order to give 9-(2-chloro-6-fluorobenzyl)-6-dimethylaminopurine as colorless crystals (385 mg), m.p. 135°–136° C.

EXAMPLE 25

In acetone (10 ml) was suspended 6-methylaminopurine sodium salt (1.291 g, 7 mmols; purity 93%) followed by addition of a solution of 2-chloro-6-fluorobenzyl chloride (1.253 g, 7 mmols) and trioctylmethylammonium chloride (141 mg, 0.35 mmol) in acetone (5 ml). The mixture was stirred at room temperature for 6 hours. Thereafter the same procedure as that described in Example 22 was followed to obtain crystals of 2-chloro-6-fluorobenzyl-substituted 6-methylaminopurine (1.510 g, yield 74%). 9-isomer 80%, 3-isomer 23%.

From the mother liquor, there were obtained crystals of 2-chloro-6-fluorobenzyl-substituted 6-methylaminopurine (313 mg, yield 15%). 9-isomer 85%, 3-isomer 8%.

EXAMPLE 26

In toluene (10 ml) was suspended 6-methylaminopurine sodium salt (1.279 g, 7 mmols; purity 94%) followed by addition of a solution of 2-chloro-6-fluorobenzyl chloride (1.253 g, 7 mmols) and trioctylmethylammonium chloride (141 mg, 0.35 mmol) in toluene (5 ml). The mixture was refluxed with stirring for 6 hours. Thereafter the same procedure as that described in Example 19 was followed to obtain crystals of 2-chloro-6-fluorobenzyl-substituted 6-methylaminopurine (1.634 g, yield 80%). 9-isomer 50%, 3-isomer 47%.

EXAMPLE 27

Removal of 3-(2-chloro-6-fluorobenzyl)-6-methylaminopurine by extraction with acetic acid In glacial acetic acid (1 ml) was dissolved 2-chloro-6-fluorobenzyl-substituted 6-methylaminopurine (500 mg; 9-isomer 71%, 3-isomer 30%) under heating, and the small amount of insoluble matter was removed by filtration. To water (4 ml) heated 90°–95° C. was added the filtrate with vigorous stirring. After stirring for 30 minutes, the mixture was cooled to room temperature. The resultant crystals were collected by filtration and washed with glacial acetic acid-water (1:4) and water in that order to give 2-chloro-6-fluorobenzyl-substituted 6-methylaminopurine as colorless crystals (343 mg). 9-isomer 93%, 3-isomer 2%.

EXAMPLE 28

In 2 N NaOH (4 ml) was dissolved 6-dimethylaminopurine (1.305 g, 8 mmols). Thereafter the same procedure as that described in Example 13 was followed to obtain 6-dimethylaminopurine sodium salt as a crystalline powder (1.585 g, purity 93%), m.p.>300° C.

EXAMPLE 29

In acetone (10 ml) was suspended 6-dimethylaminopurine sodium salt (1.388 g, 7 mmols; purity 93%) and a solution of 2-chloro-6-fluorobenzyl chloride (1.253 g, 7 mmols) and trioctylmethylammonium chloride (141 mg, 0.35 mmol) in acetone (5 ml) was added. Thereafter the same procedure as that described in Example 19 was followed to obtain crystals of 2-chloro-6-fluorobenzyl-substituted 6-dimethylaminopurine (1.273 g, yield 60%). 9-isomer 99.5%.

From the mother liquor, there were obtained crystals of 2-chloro-6-fluorobenzyl-substituted 6-dimethylaminopurine (714 mg, yield 33%). 9-isomer 42%.

The crystals (1.00 g; 9-isomer 99.5%) obtained in the above procedure was suspended in toluene (2 ml), and conc. sulfuric acid (2 ml) was added under ice-cooling with stirring. Thereafter the same procedure as that described in Example 13 was followed to obtain 9-(2-chloro-6-fluorobenzyl)-6-dimethylaminopurine as colorless crystals (927 mg).

EXAMPLE 30

In methanol (20 ml) was suspended 5% palladium on carbon (200 mg) and the suspension was shaken in hydrogen gas stream. To this suspension was added a solution of 4-amino-6-methylamino-5-phenylazopyrimidine (388 mg, 1.7 mmols) in methanol (20 ml) and the mixture was shaken in hydrogen gas stream. The catalyst was filtered off and the filtrate was concentrated under reduced pressure. The residue was dissolved in ethanol and the solution was concentrated to dryness under reduced pressure. Petroleum ether was added and the resultant crystals were collected by filtration. The crystals were put in a mixed solution of acetic anhydride (4 ml) and ethyl orthoformate (4 ml), and refluxed with stirring for 3 hours. The reaction mixture was concentrated to dryness under reduced pressure. To the residue was added 2 N NaOH (4 ml) and the mixture was refluxed with stirring for 1 hour. After cooling, the mixture was adjusted to pH 5 by addition of acetic acid, and the insoluble matter was filtered off. The filtrate was concentrated under reduced pressure and the resultant crude crystals were collected by filtration. The crystals were washed with cold water and recrystallized from water to give 6-methylaminopurine as colorless crystals (85 mg, yield 34%), m.p.>300° C.

What is claimed is:

1. 6-(2-chloro-6-fluorobenzyl)amino-4-methylamino-5-phenylazopyrimidine or an acid addition salt thereof.

* * * * *